(12) United States Patent
Wuepper

(10) Patent No.: US 9,333,285 B2
(45) Date of Patent: May 10, 2016

(54) METHOD AND DEVICE FOR DOWNGRADING AT LEAST ONE COMPONENT OF A FLUID MEDIUM

(75) Inventor: Andreas Wuepper, Frankurt (DE)

(73) Assignee: FRESENIUS MEDICAL CARE DEUSTSCHLAND GMBH, Bad Homburg (DE)

( * ) Notice: Subject to any disclaimer, the term of this patent is extended or adjusted under 35 U.S.C. 154(b) by 519 days.

(21) Appl. No.: 11/667,661

(22) PCT Filed: Nov. 11, 2005

(86) PCT No.: PCT/EP2005/012110
§ 371 (c)(1),
(2), (4) Date: May 14, 2007

(87) PCT Pub. No.: WO2006/050970
PCT Pub. Date: May 18, 2006

(65) Prior Publication Data
US 2008/0011682 A1 Jan. 17, 2008

(51) Int. Cl.
*A61M 1/34* (2006.01)

(52) U.S. Cl.
CPC ........... *A61M 1/3413* (2013.01); *A61M 1/3417* (2014.02); *A61M 1/3437* (2014.02); *A61M 1/3472* (2013.01); *A61M 1/3479* (2014.02); *A61M 1/3482* (2014.02); *A61M 1/3486* (2014.02)

(58) Field of Classification Search
USPC .............. 210/645, 646, 321, 647; 604/4, 5, 6
See application file for complete search history.

(56) References Cited

U.S. PATENT DOCUMENTS

| 4,350,594 | A | * | 9/1982 | Kawai et al. .................. 210/637 |
| 4,362,155 | A | * | 12/1982 | Skurkovich .................. 604/6.04 |
| 4,702,829 | A | * | 10/1987 | Polaschegg et al. ....... 210/195.2 |
| 6,193,681 | B1 | * | 2/2001 | Davidner et al. ............ 604/6.08 |
| 6,287,516 | B1 | * | 9/2001 | Matson et al. .................. 422/44 |
| 2004/0173530 | A1 | * | 9/2004 | Radunsky et al. ............ 210/647 |
| 2004/0182787 | A1 | | 9/2004 | Chevallet et al. |
| 2005/0281809 | A1 | * | 12/2005 | Roberts et al. ............. 424/140.1 |
| 2006/0186044 | A1 | * | 8/2006 | Nalesso ........................ 210/645 |

FOREIGN PATENT DOCUMENTS

| EP | 0 693 298 A1 | 1/1996 |
| EP | 1 348 458 A1 | 10/2003 |
| WO | WO 98/19592 | 5/1998 |
| WO | WO 2004/091694 A1 | 10/2004 |

* cited by examiner

Primary Examiner — Dirk Bass
(74) Attorney, Agent, or Firm — Jacobson Holman, PLLC.

(57) ABSTRACT

A method for the depletion of at least one component of a fluid medium includes increasing the concentration of the at least one component to be depleted before its depletion. An apparatus for the depletion of the at least one component of the fluid medium has a concentration increasing unit for increasing the concentration of the component of the fluid medium to be depleted and a depletion unit disposed downstream thereof and in fluid communication therewith for the subsequent reduction in the concentration of the component to be depleted.

22 Claims, 8 Drawing Sheets

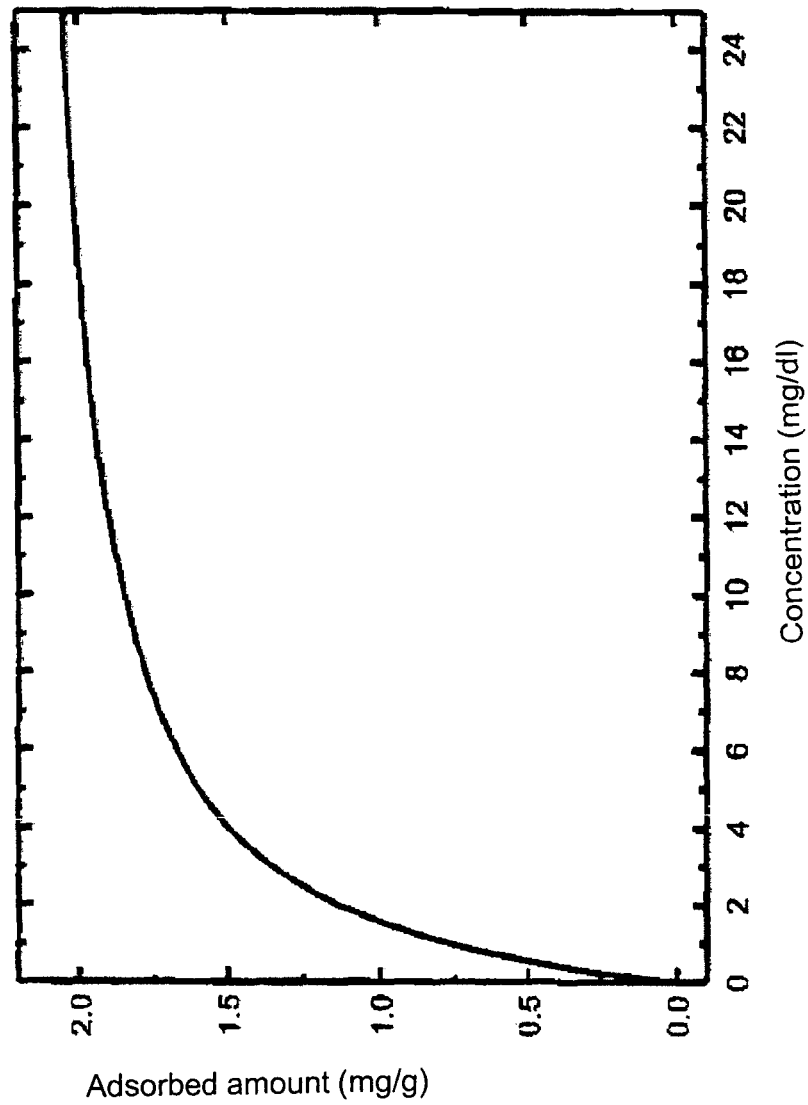

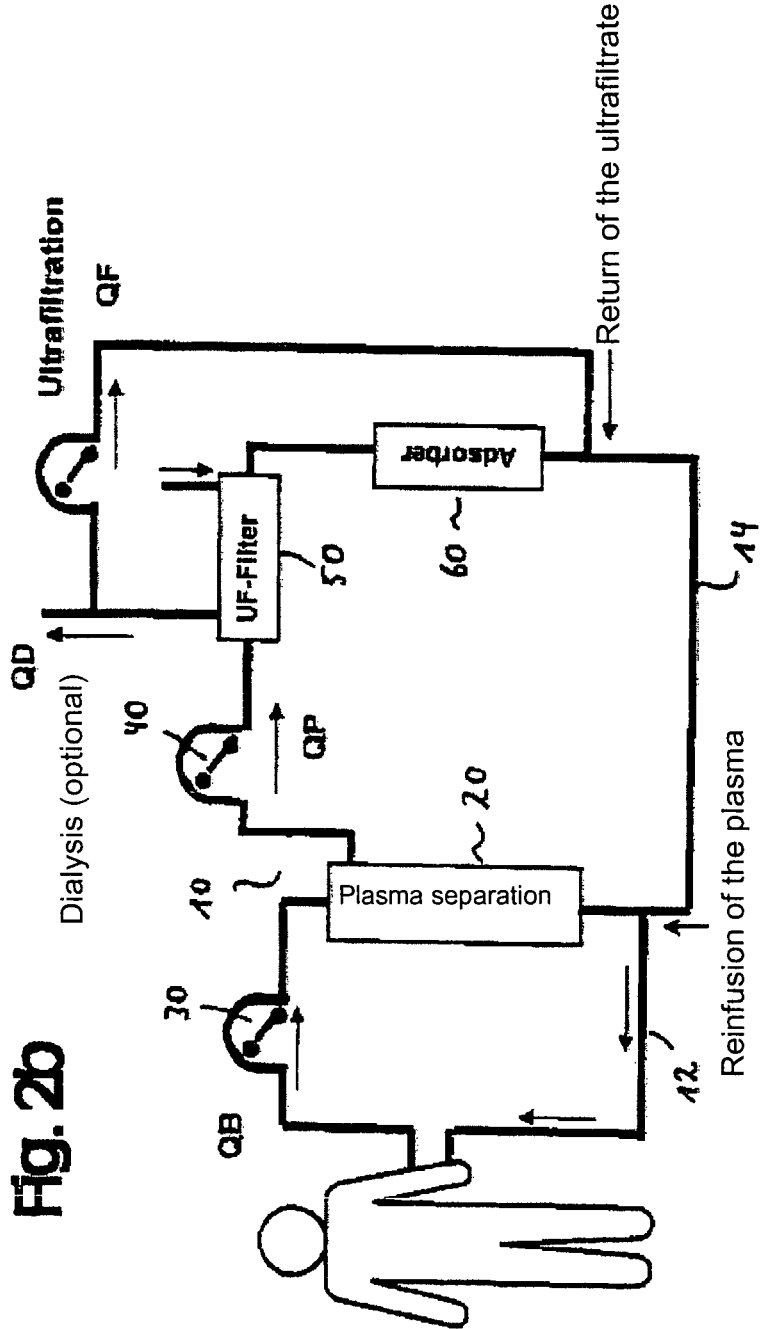

METHOD AND DEVICE FOR DOWNGRADING AT LEAST ONE COMPONENT OF A FLUID MEDIUM

CROSS-REFERENCE TO RELATED APPLICATION

This is a national stage of PCT/EP05/012110 filed Nov. 11, 2005 and published in German.

BACKGROUND OF THE INVENTION

1. Field of Invention

The present invention relates to a method and to an apparatus for the depletion of at least one component of a fluid medium. The object frequently exists of separating individual components from fluids, for example from liquid mixtures, with very different processes being able to be used for this purpose. A method for the depletion of useful materials or harmful substances is adsorption, for example, in which one or more materials of a mixture are bound to an adsorber and are separated from the further mixture components in this manner. In addition to adsorption, a plurality of other separation processes are also known, such as membrane separation processes, for example.

2. Description of the Prior Art

The aforesaid separation processes frequently have the disadvantage that their efficiency is not satisfactory or reduces in the course of the separation process. For example, the problem exists with the use of adsorbers that when there is a low load of the fluid medium with the component to be separated, they only adsorb a comparatively small amount of this component so that the efficiency of this separation process is correspondingly low in this case. The same applies accordingly, for example, to membrane processes whose efficiency at low concentrations is likewise comparatively low.

SUMMARY OF THE INVENTION

It is the object of the present invention to further develop a method and an apparatus for the depletion of at least one component of a fluid medium such that the efficiency of the depletion of this component is increased.

This object is solved by a method and an apparatus having the features described herein. Provision is accordingly made for the concentration of the at least one component to be depleted to be increased prior to its depletion. The method in accordance with the invention is thus based on concentrating the material to be depleted prior to its depletion. The means for the depletion of the component, for example the adsorber or the membrane, is thus provided with a higher concentration so that the separation of the respective component takes place correspondingly more effectively. In the case of the use of adsorbers, this is due to the fact that, in accordance with the adsorption isotherm, a higher concentration of the respective component in the fluid medium results in a correspondingly higher load of the adsorber with this component. In the case of the use of a membrane process or of other separation processes, the increased concentration of the component to be depleted likewise results in a more effective separation. The method in accordance with the invention and the apparatus in accordance with the invention can be used for any desired depletion methods.

The fluid medium can be a liquid. It is, for example, blood or blood plasma.

The increase in the concentration of the component to be depleted can take place by means of any desired separation process. Separation methods based, for example, on the setting of a thermodynamic phase equilibrium and/or also membrane methods, preferably filtration or ultrafiltration, can be considered. Examples for the first group are physiochemical separation processes such as adsorption (as non-specific bonding) as well as the specific bonding to antibodies (chemosorption).

Provision is made in a further preferred aspect of the invention for the medium separated for the purpose of the concentration increase to be supplied back to the fluid medium after the depletion of the component or for a substitution medium to be supplied to the fluid medium after the depletion of the component. The advantage of the return of the medium or of the supply of the substitution medium is above all the maintenance of volume. It can be achieved in both cases that the concentration of components which are not depleted is not changed or is hardly changed overall by the process. Accordingly, a further development of the invention consists of the fact that the fluid medium contains at least one component which is not depleted on the depletion of the component to be depleted and that the medium separated on the concentration increase of the component to be depleted or the substitution medium is supplied in an amount such that the concentration of the non-depleted component of the fluid medium after the addition of the separated medium or the substitution medium approximately corresponds to the concentration of this component prior to the increase in concentration.

It is, however, also conceivable that the concentration of the non-depleted medium after the addition of the separated medium or of the substitution medium does not correspond to the concentration of this component before the increase in concentration. Whether the concentration of the non-depleted components remains unchanged or changes overall depends on the substance.

It is generally possible that overall only the concentration of the component to be depleted is reduced, whereas the concentrations of the further components do not undergo any change overall by the process.

The depletion of the component to be depleted can take place by means of any desired process. Physio-chemical and mechanical separation processes can e.g. be considered. Examples are extraction, absorption, adsorption or also membrane processes such as dialysis.

Provision is made in a further aspect of the invention for the process to be carried out in an extracorporeal circuit. A plasma filter can be provided in the extracorporeal circuit, with the fluid medium being able to be blood plasma separated from the blood in the plasma filter or fractioned plasma. A filter can thus also be used which allows fractioned plasma past such as, for example, a filter commercially available under the trademark "ALBUFLOW" which allows albumin through, but holds immunoglobulins back). An adsorption therapy of the plasma can be carried out in this manner using the method in accordance with the invention or the apparatus in accordance with the invention.

Provision is made in a further aspect of the invention for the concentration increase of the component to be depleted to be carried out by means of ultrafiltration and for the ultrafilter to be utilized for the dialysis. If an elimination of small-molecular substances by dialysis is necessary, such as is the case with liver support therapy, the ultrafilter can accordingly optionally also be co-used for the dialysis.

Provision is made in a further aspect of the invention for the fluid medium to be blood or blood plasma and for the at least one component to be depleted to be an albumin-bound substance, immunoglobulins, interleukin or LDL cholesterol (low-density lipoprotein cholesterol).

The invention further relates to an apparatus for the depletion of at least one component of a fluid medium which comprises a concentration increasing unit for increasing the concentration of the component of the fluid medium to be depleted and a depletion unit disposed downstream thereof and in fluid communication therewith for the subsequent reduction in the concentration of the component to be depleted. The concentration increasing unit and/or the depletion unit can be configured, for example, as a separation apparatus whose separation effect is based on the setting of a thermodynamic phase equilibrium or as a membrane separation apparatus. The use of e.g. an extractor, an absorber, an adsorber or a filter/ultrafilter can be considered. The concentration increasing unit can be configured, for example, as a filter, preferably as an ultrafilter. If the membrane apparatus is the depletion unit, it can be configured, for example, as a dialyzer. The use of an adsorber as the depletion unit is likewise preferred.

Provision is made in a further aspect of the invention for the apparatus furthermore to include an extracorporeal circuit for the conducting of blood or of one or several blood components, with the concentration increasing unit and the depletion unit being arranged in the extracorporeal circuit.

A line which opens into the extracorporeal circuit downstream of the depletion unit can branch off from the concentration increasing unit. This line serves for the supply of the medium separated in the concentration increase, for example the supply of the filtrate, to the blood or blood plasma after the depletion of the component to be depleted.

Provision can furthermore be made for a line which is in fluid communication with a source of a substitution medium to open into the extracorporeal circuit downstream of the depletion unit. It is thus possible to return the medium separated on the increase in concentration not to the blood/blood plasma, but rather to replace it by a substitution liquid.

A combination of both aforesaid procedures is also imaginable.

In a preferred aspect of the invention, the extracorporeal circuit has a first circuit and a second circuit, with the first circuit being in fluid communication with or being connectable to a patient and with the second circuit being in communication with the first circuit by means of a plasma filter and including the concentration increasing unit and the depletion unit. An arrangement of this type serves the purpose of subjecting the plasma gained from the blood by means of the plasma filter to an adsorption therapy, with a concentration increase, preferably by ultrafiltration, taking place in accordance with the invention before the adsorption.

Provision can furthermore be made for a dialysate circuit to be connected or to be connectable to the concentration increasing unit. If this is an ultrafilter, it can additionally be used for dialysis. In this case, blood or blood plasma flows through the ultrafilter on the one side of the membrane and dialysate flows through the ultrafilter on the other side of the membrane.

BRIEF DESCRIPTION OF THE DRAWINGS

Further details and advantages of the invention will be explained in more detail with reference to an embodiment shown in the drawing. There are shown:

FIG. 1 adsorption isotherm: adsorbed amount of the component as a function of the concentration of this component in the liquid;

FIGS. 2a, 2b: a process diagram of "ultra-absorption" with return of the ultrafiltrate;

DETAILED DESCRIPTION OF THE PERFERRED EMBODIMENTS

Figure 2A:
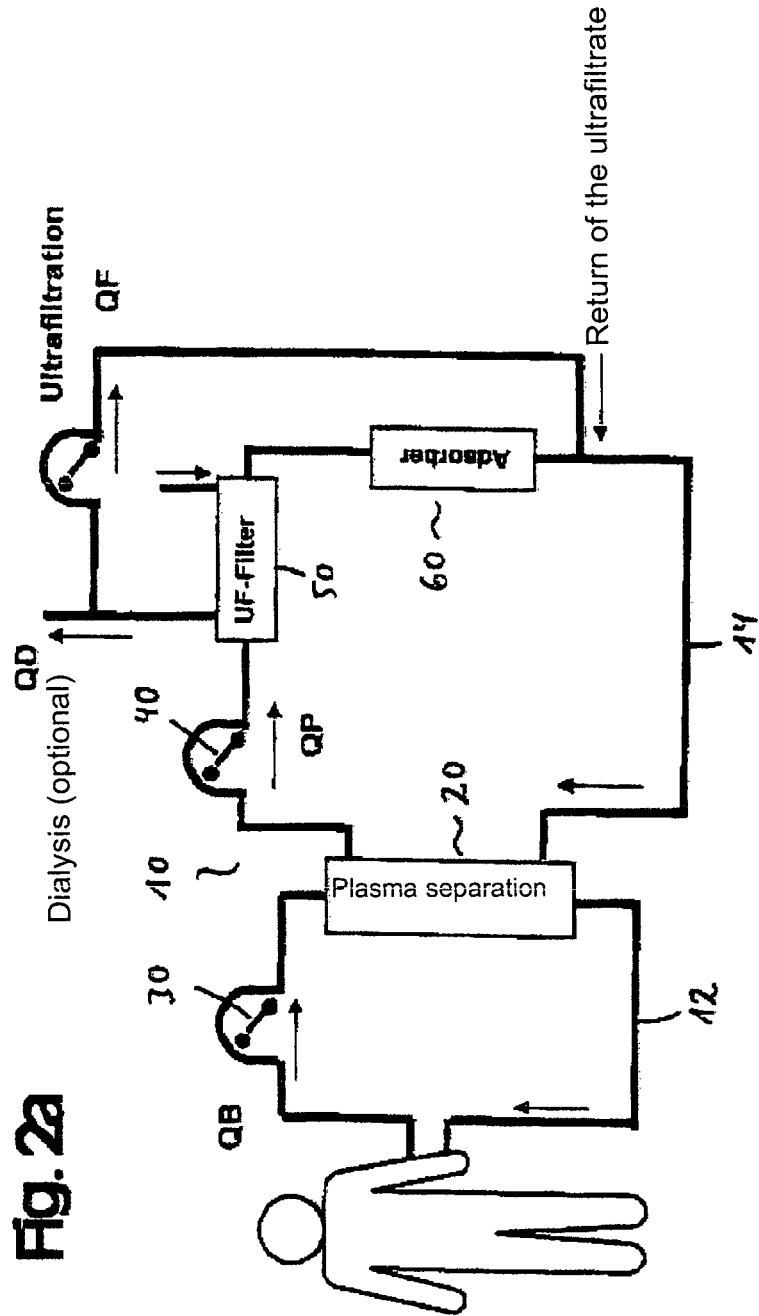

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

FIG. 1 shows the so-called adsorption isotherm which reproduces the amount adsorbed on an adsorber in dependence on the concentration of the respective component in the solution.

Adsorbers serve, for example, for extracorporeal blood purification and, in this connection, for the elimination of substances which cannot be removed by dialysis and hemofiltration. Dialysis and hemofiltration remove substances which are soluble in water and have a molecular weight which is below the exclusion limit of the dialyzer or the hemofilter. This exclusion limit (<60 kD) is selected such that albumin, the main protein of blood, is held back.

As stated above, adsorption processes serve the purification of blood from substances which are albumin-bound or which cannot be removed or can only be removed insufficiently by dialysis or hemofiltration due to their high molecular weight. Substances which are removed by adsorption instead of by dialysis due to their high molecular weight are, for example, LDL (treatment of hypercholesterolemia) and immunoglobulins (treatment of auto-immune diseases, transplant pre-care). The albumin-bound substances are, for example, the water insoluble bilirubin which is transported in the blood while bound to albumin. It can only be removed by absorptive processes which are used, for example, in liver support therapy.

As can be seen from FIG. 1, the substance amount which can be bound by an adsorber is dependent on the concentration of the substance to be adsorbed in the solution, for example in the blood or in the plasma. It can be seen from the adsorption isotherm in accordance with FIG. 1 that, at higher concentrations, larger loads are also present, i.e. larger amounts can be bound to the adsorber. An increase in concentration in particular results in a substantial change in the adsorbed amount when the concentration lies in the strongly increasing part of the curve.

It can be observed in the course of a treatment with adsorbers that the removal performance, i.e. the clearance, falls off. One reason for this is the increasing load of the adsorber. The clearance has, however, very frequently fallen off a lot even before the maximum load of the adsorber has been reached. This is due to the fact that the concentration in the substance to be purified in the fluid medium, for example in the blood or plasma, has fallen into the range of the high gradient of the adsorption isotherm so that the adsorbed amount is accordingly likewise small.

The method in accordance with the invention or the apparatus in accordance with the invention are based on concentrating the substance to be depleted or the substance to be adsorbed in the fluid, for example in the blood or in the plasma, before the depletion. In an embodiment of the invention, the depletion takes place by adsorption and the concentration takes place by ultrafiltration. It can be achieved in this manner that the adsorber is presented with a higher concentration so that the adsorption in accordance with FIG. 1 takes place more effectively since the concentration results in a higher load of the adsorber.

FIG. 2a shows a process diagram of the combination of ultrafiltration and adsorption ("ultra-adsorption). As can be seen from FIG. 2, the extracorporeal circuit 10 comprises a first circuit 12 and a second circuit 14. Both circuits 12, 14 are connected to one another by the plasma filter 20. Blood plasma is removed from the blood flowing out of the first circuit 12 in the plasma filter 20. The blood plasma circulates through the second circuit 14.

The circulation of the blood in the first circuit 12 takes place by means of the blood pump 30. The circulation of the blood plasma in the second circuit 14 takes place by means of the plasma pump 40. As can be seen from FIG. 2a, the ultrafilter 50 is located in the second circuit 14. The adsorber 60 is connected downstream of it. A concentration of the plasma, and thus also an increase in the concentration of the component to be depleted, such as bilirubin, takes place in the ultrafilter 50. The adsorber 60 is thus charged with a concentrated solution, which has the result that the separation of the component to be depleted takes place more effectively due to the higher adsorbed amount in accordance with the adsorption isotherm of FIG. 1.

As can furthermore be seen from FIG. 2a, the ultrafiltrate gained in the ultrafilter 50 during the ultrafiltration is supplied back to the second circuit 14 by means of a pump and of an ultrafiltration line downstream of the adsorber 60. A volume maintenance is thereby achieved. It can furthermore be achieved in this manner that the concentration of at least some of the components not depleted in the adsorber 60 is not changed over all, i.e. the increase in concentration in the ultrafilter 50 is followed by a corresponding dilution. Whether a change in concentration occurs is substantially dependent on the substance.

Alternatively to the system shown in FIG. 2a, it is possible to reinfuse the plasma in the second circuit 14 directly into the first circuit 12, as is shown in FIG. 2b.

FIG. 2b shows a variant of the process diagram shown in FIG. 2a ("reinfusion"). The first circuit 12. and the second circuit 14 are only separated upstream by the plasma filter 20. Downstream, a direct infusion of the blood plasma of the second circuit 14 into the whole blood of the first circuit 12 takes place. This variant has the advantage over the variant shown in FIG. 2a that the amount of the plasma crossing from the first circuit-12 into the-second circuit 14 can be controlled by the plasma pump 40. In the method shown in FIG. 2a ("recirculation"), the transfer of loaded plasma from the first circuit 12 into the second circuit 14 or of depleted plasma from the second circuit 14 into the first circuit 12 takes place in a purely passive manner and substantially independently of the delivery rate of the plasma pump 40.

In the method variant "reinfusion" in accordance with FIG. 2b, further safety measures are required to prevent a crossover of adsorber material into the systematic blood circuit of the patient in the event of a first error "leaking adsorber cartridge". These safety measures are not shown separately here.

Figure 3:
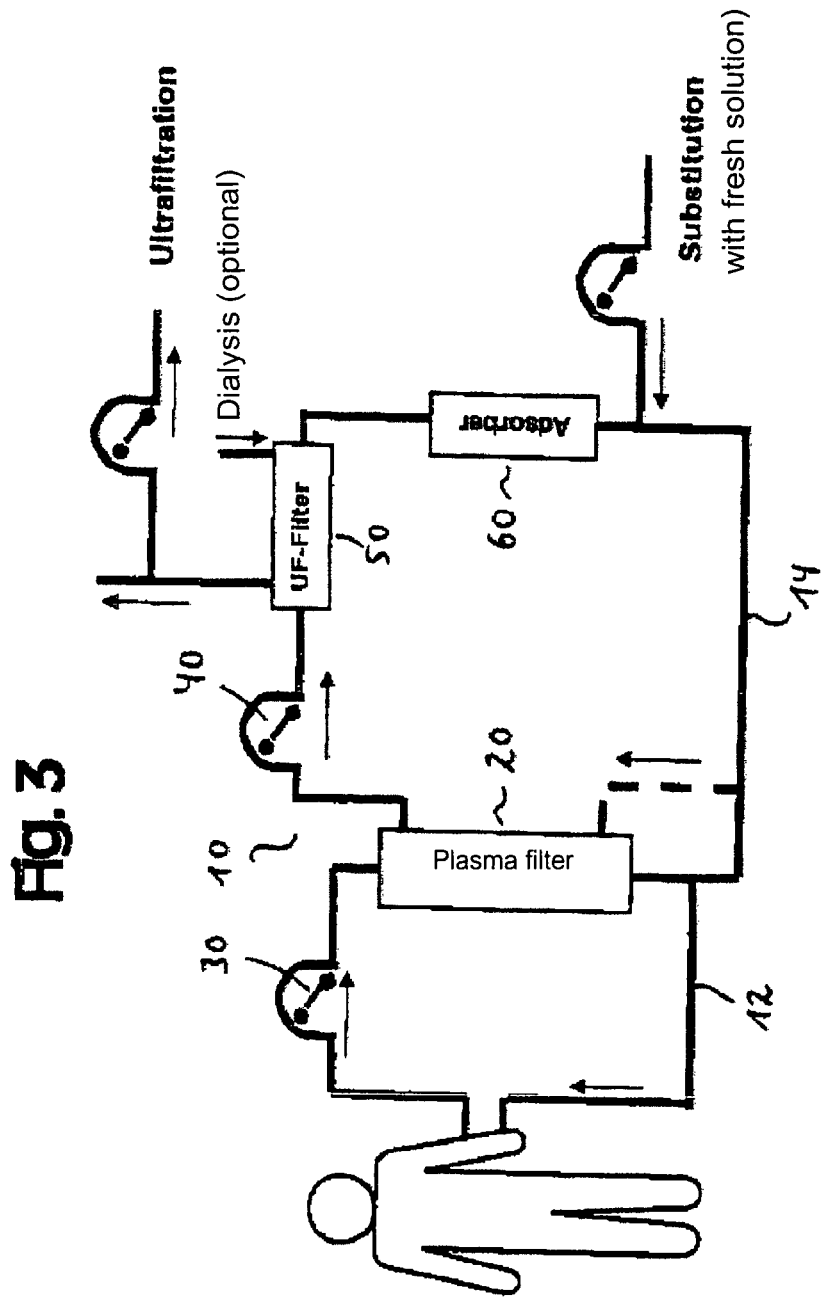
FIG. 3: a process diagram of "ultra-adsorption" with supply of fresh substitution solution.

Alternatively to the arrangement shown in FIGS. 2a, 2b, it is conceivable in accordance with FIG. 3 to discard the ultrafiltrate and to add fresh substitution solution downstream of the adsorber, as is shown in FIG. 3.

The removed ultrafiltrate can thus either be supplied back to the blood or plasma or be replaced by a substitution solution. A combination of both possibilities is also conceivable.

FIG. 3 shows the two variants "recirculation and reinfusion" as alternative flow paths. In this respect, we refer to the above explanations on FIGS. 2a, 2b.

Figure 4:
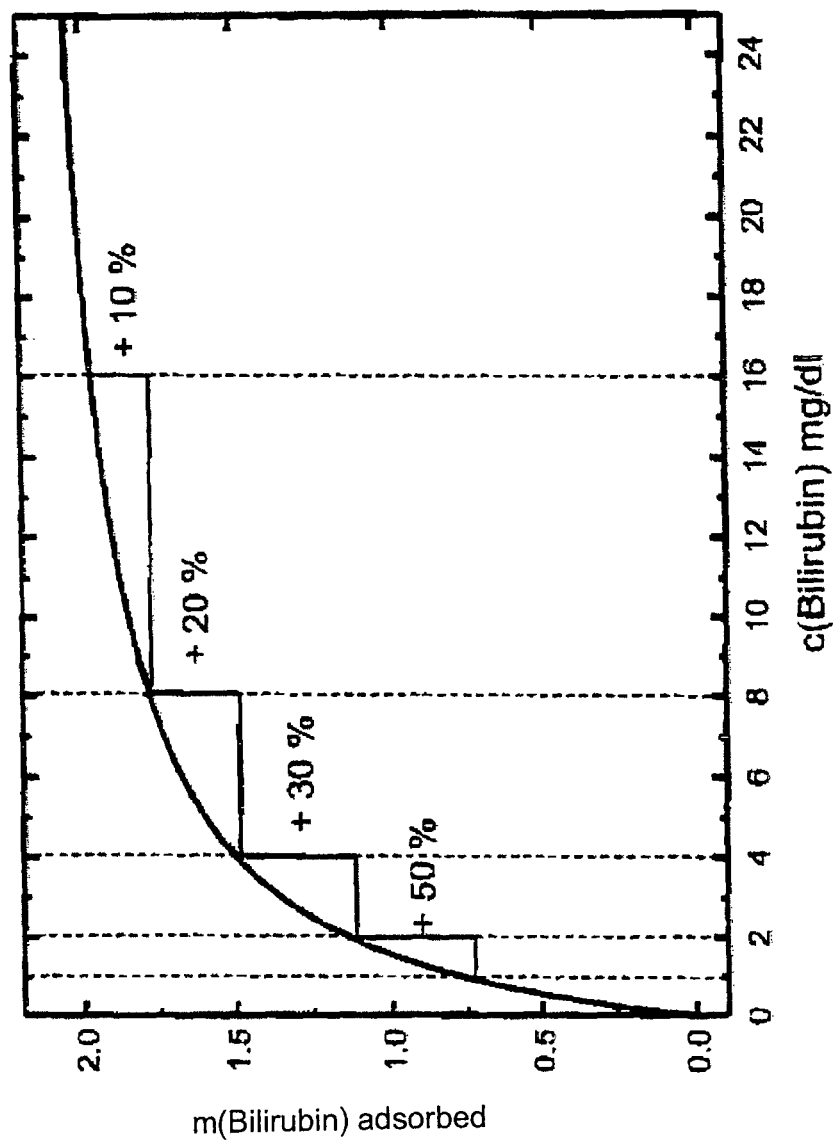
FIG. 4: explanation of the effect of the ultrafiltration-amplified adsorption with reference to the adsorption isotherm.

FIG. 4 shows the theoretical effect of the ultrafiltration-amplified adsorption. The effect is shown in FIG. 4 which an increase in concentration effects by the factor of 2 on the adsorbed amount in the case of bilirubin and a known adsorber. If the concentration in the plasma is at 8 mg/dl and if the bilirubin is concentrated to 16 mg/dl by the ultrafiltration, the adsorber can adsorb 10% more bilirubin.

As can be seen from FIG. 4, the increase in the adsorption performance rises as the concentration of the bilirubin falls. If the concentration in the plasma is e.g. at 4 mg/dl due to a decrease during the treatment, an increase by the factor of 2 effects a rise in the adsorbed amount by 20%. On a concentration increase of 1 mg/dl to 2 mg/dl, the effect even amounts to 50%.

If the therapy also requires an elimination of small-molecular substances by dialysis, such as this the case in liver support therapy, the ultrafilter can optionally also be co-used for dialysis. This is indicated in the FIGS. 2a, 2b and 3. In this case, the ultrafilter not only serves the concentration of the components not separated in the ultrafilter, but also the separation of small molecular substances from the plasma. Blood plasma thus flows through the ultrafilter on one side of the membrane and dialysate flows through the ultrafilter on the other side.

Figure 5:
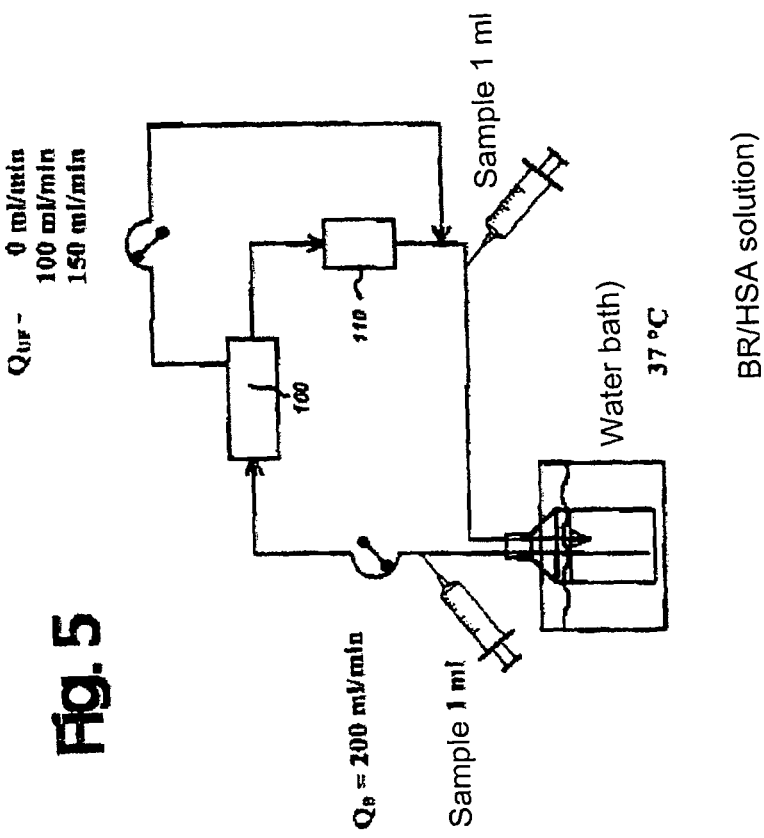
FIG. 5: a schematic representation of the trial setup for the determination of the effect of the increase in concentration of a component before its depletion.

FIG. 5 shows the diagram of the trial setup for the verification of the described effect of the concentration of the component to be depleted. The setup of the arrangement and the carrying out of the trial carried out using the arrangement of FIG. 5 takes place as follows:

In each case 1000 ml of a BR/HSA solution (BR=bilirubin; HSA=human serum albumin) with a BR concentration of 15 mg/dl and an HSA concentration of 30 g/l were recirculated over an adsorber cartridge with a flow of $Q_B$=200 ml/min for three hours. The BR/HSA solution was concentrated before the adsorber cartridge 110 by means of filtration by the high-flux dialyzer 100. The filtrate was supplied to the circuit again after the adsorber cartridge 110, as is shown in FIG. 5.

Three trials were carried out with different filtration flow types $Q_{UF}$. The first trial was carried out with $Q_{UF}$=0 ml/min and served as a control trial. In the second trial, the solution led through the adsorber was concentrated approximately by the factor of 2 with $Q_{UF}$=100 ml/min. In the third trial approximately by the factor of 4 with $U_{UF}$=150 ml/min.

A BR/HSA solution was first prepared such that, after supply of the filling volume of the adsorber cartridge 110, a BR concentration of 15 mg/dl and an HSA concentration of 30 g/l were reached. For this purpose, first, 150 mg BR was dissolved in 20 ml 0.1 N NaOH while stirring. After complete dissolving of the BR, 150 ml 20% HSA solution was added and stirred at room temperature for an hour. Subsequently, 760 ml aqueous solution 0.01 N phosphate buffer solution (pH 7.4) was added at 110 mM NaCl and heated to 37° C. in the water bath.

Before the start of the trials, the adsorber cartridge 110 was flushed with 1000 ml isotonic saline solution, with in each case the last approx. 70 ml remaining as filling volume in the adsorber cartridge 110. At the start of the trials, the circuit was first filled up to the level of the filling volume of the adsorber capsule and the filtrate circuit was filled with BR/HSA solution or filtrate. Then the trials were started, with the first samples being taken on the first visible yellowing of the solution exiting the adsorber 110 and with the time being set to 0.1 ml samples were taken in each case every 15 minutes before and after the adsorber cartridge from the region of the circuit not concentrated, as is indicated in FIG. 5. In the third trial with the highest ultrafiltration rate $Q_{UF}$=150 ml/min, samples were taken every 5 minutes in the first 30 minutes.

The composition of the 1000 ml BR/HSA solution is as follows:
150 mg bilirubin
20 ml 0.1 N NaOH
150 ml 20% HSA solution
760 ml aqueous 0.01 N phosphate buffer solution pH 7.4 with 110 mM NaCl
approx. 70 ml isotonic NaCl solution (adsorber filling volume)

The composition of 2000 ml 0.01 N phosphate buffer with 110 mM NaCl is as follows:
0.502 g $NaH_2PO_4$ $H_2O$
5.860 g $Na_2HPO_4H_2O$
12.860 g NaCl
2000 ml $H_2O$.

Figure 6:
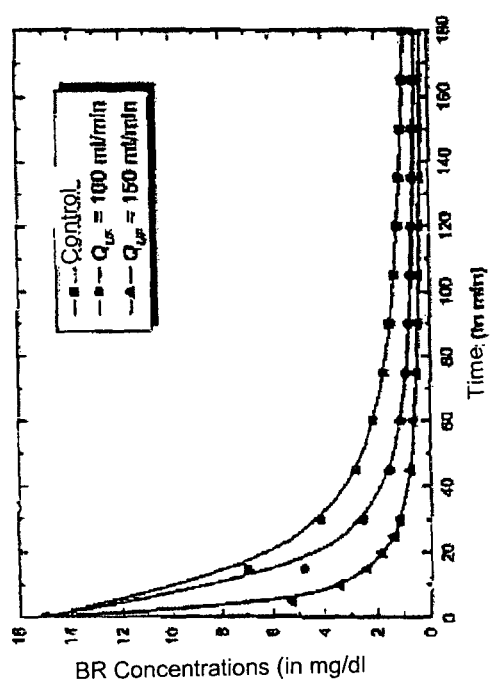
FIG. 6: a representation of the bilirubin concentration in dependence on the time for different ultrafiltration rates.

FIG. 6 shows the bilirubin concentrations of the samples taken in front of the adsorber cartridge in dependence on the trial duration. The theoretical starting concentration value of bilirubin of 15 mg/dl was used at the time t=0 minutes. The measured time was not used since there was still no sufficient mixing of the BR/HSA solution with the NaCl solution present in the absorber 110 at the time t=0.

Figure 7:
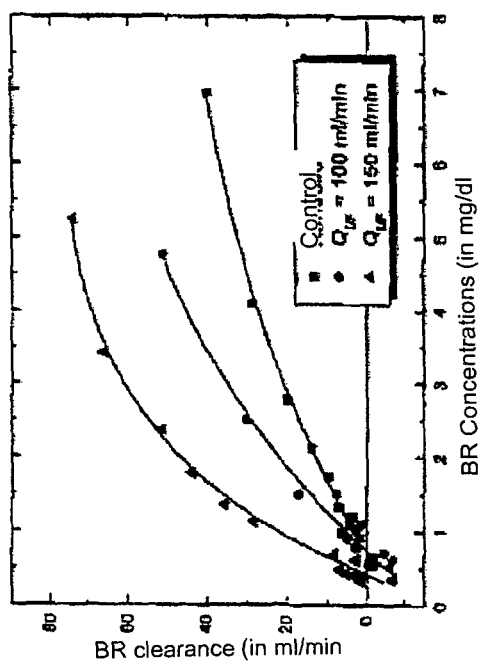
FIG. 7: a representation of the bilirubin clearance in dependence on the bilirubin concentration for different ultrafiltration rates.

As can be seen from FIG. 6, as the concentration increases, i.e. as the ultrafiltration rate rises, a clear acceleration of the reduction of the bilirubin concentration can be recognized, i.e. an improvement in the purification performance by concentration before the adsorption. FIG. 7 shows the clearance for bilirubin based on the results in accordance with FIG. 6 in dependence on the bilirubin concentration of the samples taken before the adsorber cartridge 110. The clearance values calculated from the respective first samples in time were not taken into account since there was still no sufficient mixing of the BR/HSA solution with the NaCl solution of the filling volume of the adsorber 110. The values were fitted by means of an exponential function of the 1st order.

It can be recognized in accordance with the trial results of FIG. 6 that the clearance of the adsorber, i.e. its purification performance, increases as the ultrafiltration rate rises, i.e. as the concentration of the species to be depleted rises.

The method in accordance with the invention and the apparatus in accordance with the invention can generally be used for any desired depletion processes outside of medical engineering and also in the sphere of medical engineering. Possible applications are adsorption processes as well as other depletion processes such as dialysis.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method for the depletion of at least one component of blood or blood plasma, comprising in the following order the steps of:

conducting the blood or blood plasma in an extracorporeal circuit that includes a concentration increasing unit and a depletion unit, the extracorporeal circuit having a first circuit and a second circuit, the first circuit being in fluid communication with or being connectable to a patient, and the second circuit being in communication with the first circuit by a plasma filter and including the concentration increasing unit and the depletion unit;

increasing an efficiency of the depletion of the at least one component by first increasing a concentration of the at least one component to be depleted in the blood or blood plasma before the depletion of said component, the step of increasing the concentration including separating in the concentration increasing unit a first portion of the blood or blood plasma from a second portion of the blood or blood plasma that contains the increased concentration of the at least one component to be depleted;

supplying to the depletion unit the second portion of the blood of blood plasma that contains the increased concentration of the at least one component to be depleted; and supplying, downstream of the depletion unit, the separated first portion of the blood or blood plasma back to the second portion of the blood or blood plasma after the depletion of the component to be depleted therefrom, the blood or blood plasma including at least one component which is not depleted in the depletion of the component to be depleted, and the separated blood or blood plasma being supplied to the blood or blood plasma after the depletion in an amount such that a concentration of the non-depleted component of the blood or blood plasma after addition of the separated blood or blood plasma approximately corresponds to the concentration of the non-depleted component before the increase in concentration.

2. The method in accordance with claim 1, wherein the step of separating is effected by at least one of setting a thermodynamic phase equilibrium and a membrane method.

3. The method in accordance with claim 2, wherein the setting of the thermodynamic phase equilibrium is effected by adsorption, and the membrane method is dialysis.

4. The method in accordance with claim 1, wherein the extracorporeal circuit includes a plasma filter, and wherein the blood plasma is separated from the blood in the plasma filter, or is fractioned blood plasma.

5. The method in accordance with claim 1, wherein the step of increasing the concentration of the component to be depleted is effected by ultrafiltration and wherein an ultrafilter that effects the ultrafiltration is used for dialysis.

6. The method in accordance with claim 1, wherein the at least one component to be depleted is at least one of an albumin-bound substance, an immunoglobulin, interleukin, and LDL cholesterol (low-density lipoprotein cholesterol).

7. An apparatus for the depletion of at least one component of blood or blood plasma, comprising:

an extracorporeal circuit that is configured to conduct the blood or the blood plasma and that includes a concentration increasing unit for increasing a concentration of the component of the blood or blood plasma to be depleted and a depletion unit for subsequently reducing the concentration of the component to be depleted, the extracorporeal circuit having a first circuit and a second circuit, the first circuit being in fluid communication with or being connectable to a patient, and the second circuit being in communication with the first circuit by a plasma filter and including the concentration increasing unit and the depletion unit, the concentration increasing unit being configured such that the concentration of the component in the blood or blood plasma to be depleted is increased by separating in the concentration increasing unit a first portion of the blood or blood plasma from a second portion the blood or blood plasma that contains the increased concentration of the at least one component to be deleted, and supplying to the depletion unit the second portion of the blood of blood plasma that contains the increased concentration of the at least one component to be depleted, the depletion unit being disposed downstream of the concentration increasing unit and in fluid communication therewith, and the apparatus being configured to supply, downstream of the depletion, unit, the separated first portion of the blood or blood plasma back to the second portion of the blood or blood plasma after the depletion of the component to be depleted therefrom, the blood or blood plasma including at least one component which is not depleted in the depletion of the component to be depleted, and the separated blood or blood plasma being supplied to the blood or blood plasma after the depletion in an amount such that a concentration of the non-depleted component of the blood or blood plasma after addition of the separated blood or blood plasma approximately corresponds to the concentration of the non-depleted component before the increase in concentration.

8. The apparatus in accordance with claim 7, wherein the concentration increasing unit is configured as a separating apparatus that effects the separation by at least one of setting a thermodynamic phase equilibrium and a membrane process.

9. The apparatus in accordance with claim 7, wherein the depletion unit is configured as a separating apparatus that effects the separation by at least one of setting a thermodynamic phase equilibrium and a membrane process.

10. The apparatus in accordance with claim 7, wherein a line which opens into the extracorporeal circuit downstream of the depletion unit branches off from the concentration increasing unit.

11. The apparatus in accordance with claim 7, wherein a line opens into the extracorporeal circuit downstream of the depletion unit and is in fluid communication with a source of a substitution blood or blood plasma.

12. The apparatus in accordance with claim 7, wherein a dialysate circuit is connected to the concentration increasing unit.

13. The method according to claim 2, wherein the membrane method is at Least one of filtration and ultrafiltration.

14. The apparatus according to claim 8, wherein the separating apparatus that effects the membrane process is an ultrafilter.

15. The apparatus according to claim 9, wherein the separating apparatus is an adsorber.

16. The apparatus according to claim 9, wherein the separating apparatus that separates by the membrane process is a dialyzer.

17. A method for depleting at least one component of blood or blood plasma, comprising in the following order the steps of:

conducting the blood or blood plasma in an extracorporeal circuit having a first circuit and a second circuit in communication with each other via a plasma filter, the first circuit being configured for fluid communication with a patient, and the second circuit including a membrane filter concentration increasing unit and a depletion unit;

increasing an efficiency of depleting the component by increasing in the blood or blood plasma a concentration of the component to be depleted, the concentration increasing step including (i) conducting the blood or blood plasma through the membrane filter concentration increasing unit so as to provide (a) a component-rich blood or blood plasma portion that does not pass through the membrane filter of the membrane filter concentration increasing unit and (b) a blood or blood plasma portion that does pass through the membrane filter of the membrane filter concentration increasing unit, the component-rich blood or blood plasma portion containing the increased concentration of the at least one component to be depleted, and (ii) separating from the concentration increasing unit the portion of the blood or blood plasma that passes through the membrane filter;

conducting the component-rich blood or blood plasma portion that contains the increased concentration of the at least one component to be depleted through the depletion unit to provide a component-depleted blood or blood plasma portion; and supplying, downstream of the depletion unit, to the component-depleted blood or blood plasma portion, the separated portion of the blood or blood plasma, the blood or blood plasma including at least one component which is not depleted in the depletion of the component to be depleted, and the separated blood or blood plasma being supplied to the blood or blood plasma after the depletion in an amount such that a concentration of the non-depleted component of the blood or blood plasma after addition of the separated blood or blood plasma approximately corresponds to the concentration of the non-depleted component before the increase in concentration.

18. The method according to claim 17, wherein the at least one component is a blood component.

19. An apparatus for depleting at least one component of blood or blood plasma, comprising an extracorporeal circuit having a first circuit and a second circuit in communication with each other via a plasma filter, the first circuit being configured for fluid communication with a patient, and the second circuit including a membrane filter concentration increasing unit and a depletion unit, the membrane filter concentration increasing unit increasing an efficiency of depleting the component by first increasing in the blood or blood plasma a concentration of the at least one component to be depleted, the membrane filter concentration increasing unit being configured to process the blood. or blood plasma so as to provide (i) a component-rich blood or blood plasma portion that does not pass through the membrane filter of the membrane filter concentration increasing unit, the component-rich blood or blood plasma portion containing the increased concentration of the at least one component to be depleted, and (ii) a blood or blood plasma portion that does pass through the membrane filter of the membrane filter concentration increasing unit and that is separated from the concentration increasing unit, the depletion unit being configured to process the component-rich blood or blood plasma portion that contains the increased concentration a the at least one component to be depleted so as to provide a component-depleted blood or blood plasma portion, and the second circuit being configured to supply, downstream of the depletion unit, to the component-depleted blood or blood plasma portion, the separated portion of the blood or blood plasma, the blood or blood plasma including at least one component which is not depleted in the depletion of the component to be depleted, and the separated blood, or blood plasma being supplied to the blood or blood plasma after the depletion in an amount such that a concentration of the non-depleted component of the blood or blood plasma after addition of the separated blood or blood plasma approximately corresponds to the concentration of the non-depleted component before the increase in concentration.

20. The apparatus according to claim 19, wherein the at least one component is a blood component.

21. The method according to claim 1, further comprising a step of supplying a substitution blood or blood. plasma to the blood or blood plasma after the depletion of the component to be depleted.

22. The apparatus according to claim 7, further comprising the apparatus being configured to supply a substitution, blood or blood plasma to the blood or blood plasma after the depletion of the component to be depleted.

* * * * *